United States Patent
Holland et al.

(10) Patent No.: US 8,778,660 B2
(45) Date of Patent: Jul. 15, 2014

(54) METHOD FOR INCREASING ALGAE GROWTH AND THE USE THEREOF IN PRODUCTION OF ALGAE-DERIVED BIOFUELS AND OTHER CHEMICAL

(75) Inventors: Mark Holland, Port Washington, NY (US); Patrick Di Bello, Port Washington, NY (US); Richard M. Carlton, Port Washington, NY (US)

(73) Assignee: NewLeaf Symbiotics, Inc., St. Louis, MO (US)

( * ) Notice: Subject to any disclaimer, the term of this patent is extended or adjusted under 35 U.S.C. 154(b) by 0 days.

(21) Appl. No.: 13/064,883

(22) Filed: Apr. 22, 2011

(65) Prior Publication Data

US 2011/0269219 A1 Nov. 3, 2011

Related U.S. Application Data

(60) Provisional application No. 61/327,661, filed on Apr. 24, 2010.

(51) Int. Cl.
*C12N 1/12* (2006.01)

(52) U.S. Cl.
USPC .................................................. 435/257.6

(58) Field of Classification Search
USPC .................................................. 435/257.6
See application file for complete search history.

(56) References Cited

U.S. PATENT DOCUMENTS

| | | | |
|---|---|---|---|
| 2004/0168648 A1* | 9/2004 | Ayers .......................... | 119/200 |
| 2006/0228797 A1* | 10/2006 | Holland et al. .............. | 435/377 |
| 2008/0038290 A1* | 2/2008 | Renimel et al. ........... | 424/195.17 |
| 2008/0160591 A1* | 7/2008 | Willson et al. .............. | 435/132 |

FOREIGN PATENT DOCUMENTS

| WO | WO2008048861 | * | 4/2008 | .............. A01G 7/00 |
|---|---|---|---|---|
| WO | 2012012671 A2 | | 1/2012 | |

OTHER PUBLICATIONS

Croft et al. Algae need their vitamins. Eukaryotic Cell. 2006;5(8):1175-1183.*
De Pauw et al. Large-scale microalgae production for nursery rearing of marine bivalves. Aquacultural Engineering. 1983;2:27-47.*
Rooke et al. Energy from photobioreactors: Bioencapsulation of photosynthetically active molecules, organelles, and whole cells within biologically inert matrices. Pure Appl Chem. 2008;80(11):2345-2376.*
ScienceDaily. The secret life of algae. 2006.*
Teschler LE. Algae automation. Machine Design. 2009.*
Butane. Encyclopedia Britannica. 2012.*
Powers R. Sounding circle: Bio-fuel from algae. Bio-Fuel From Algae. 2006.*
Gouveia et al. Microalgae as a raw material for biofuels production. J nd Microbiol Biotechnol. 2009;36:269-274.*
Croft et al., "Algae Acquire Vitamin B12 Through a Symbiotic Relationship with Bacteria", Nature, 2005, pp. 90-93, vol. 438, No. 3.
Holland et al., "PPFMs and Other Covert Contaminants: Is There More to Plant Physiology Than Just Plant?", Annual Review Plant Physiology and Molecular Biology, 1994, pp. 197-209, vol. 45.
Madhaiyan et al., "Growth Promotion and Induction of Systemic Resistance in Rice Cultivar Co-47 (*Oryza sativa* L.) by *Methylobacterium* spp.", Botanical Bulletin of Academia Sinica, 2004, pp. 315-324, vol. 45.
Da Silva et al., "Oil Production Towards Biofuel from Autotrophic Microalgae Semicontinuous Cultivations Monitorized by Flow Cytometry", Applied Biochemistry and Biotechnology, 2009, pp. 568-578, vol. 159.
Kaladharan et al., Laboratory Culture of *Gracilaria* spp. and *Ulva lactuca* in Seawater Enriched Media, Seaweed Research and Utilisation, 2003, pp. 139-142, vol. 25 (1 & 2).
Li et al., "Effects of Nitrogen Sources on Cell Growth and Lipid Accumulation of Green Alga *Neochloris oleoabundans*", Applied Microbiology and Biotechnology, 2008, pp. 629-636, vol. 81.
Pruvost et al., "Investigation of Biomass and Lipids Production with *Neochloris oleoabundans* in Photobioreactor", Bioresource Technology, 2009, pp. 5988-5995, vol. 100.
Tournabene et al., "Lipid Composition of the Nitrogen Starved Green Alga *Neochloris oleoabundans*", Enzyme and Microbial Technology, 1983, pp. 435-440, vol. 5.
Wahal et al., "Maximizing Algal Growth in Batch Reactors Using Sequential Change in Light Intensity", Applied Biochemistry and Biotechnology, 2010, pp. 511-522, vol. 161.
Wang, "Microalgal Lipids Production and N/P Removal Using the Green Alga *Neochloris oleoabundans*", 2010, MASc Thesis, Department of Chemical and Biological Engineering, University of Ottawa, Canada.

* cited by examiner

*Primary Examiner* — Ruth Davis
*Assistant Examiner* — Lynn Y Fan
(74) *Attorney, Agent, or Firm* — Thompson Coburn LLP; Charles P. Romano

(57) ABSTRACT

A method of increasing yield of cultivated algae, which entails the step of cultivating one or more species of algae in the presence of one or more species of PPFM bacteria, for at least a portion of the algae cultivation.

22 Claims, 9 Drawing Sheets

METHOD FOR INCREASING ALGAE GROWTH AND THE USE THEREOF IN PRODUCTION OF ALGAE-DERIVED BIOFUELS AND OTHER CHEMICAL

BACKGROUND OF THE INVENTION

1. Field of the Invention

The present invention relates to methods for increasing or stimulating algae growth, and increasing thereby the number of molecules of the various chemicals of value that algae can produce, including but not limited to biofuels.

2. Description of the Background

It is known that Pink-Pigmented Facultative Methylotrophs (PPFM bacteria), for example but not limited to, *Methylobacterium mesophilicum* and related species, are associated with essentially all land plants, and that PPFM bacteria can be manipulated or selected to stimulate the growth of land plants. Additionally, it is also known that PPFM can be manipulated or selected to produce substances, such as vitamin B12, which when secreted onto land plants afford land plants, such as lettuce, to have enhanced nutritional value for humans.

Currently, much biofuel is produced by extraction from foodstuffs, with corn in the United States and sugar cane in Brazil being common examples. However, there is a growing consensus that it would be more prudent to use non-foodstuffs as the raw material for microbial fermentation to produce biofuels. A primary reason for this is the upward pressure on grain and food prices due to the increased demand for corn. It has been found that the upward pressure on corn prices has a similar, albeit diminished, effect on all grains sold in the world markets. Some have argued with basis that this can lead to food shortages with consequent riots and negative implications for U.S. national security.

While attempts have been made to use some non-foodstuffs, such as algae and cellulosic materials, as raw materials for microbial fermentation to make biofuel, it has proved difficult to obtain significant yields with these raw materials. Hence, a need exists for methods that make such fermentations or other propagation methods more commercially feasible.

SUMMARY OF THE INVENTION

Accordingly, it is an object of the present invention to provide a method for increasing algae growth.

It is also an object of the present invention to stimulate algae growth by cultivating algae in the presence of PPFM bacteria.

Further, it is an object of the present invention to provide a method for increasing production of the valuable chemicals that algae are capable of producing, whether naturally or by genetic engineering. Examples of such chemicals include, but are not limited to biofuels, e.g. neutral lipids (oils), ethanol and butane as well as DHA and astaxanthin.

Accordingly, the above objects and others are provided by a method for stimulating algae growth, which entails the step of cultivating the algae in the presence of PPFM bacteria.

DETAILED DESCRIPTION OF THE PREFERRED EMBODIMENTS

Figure 1:
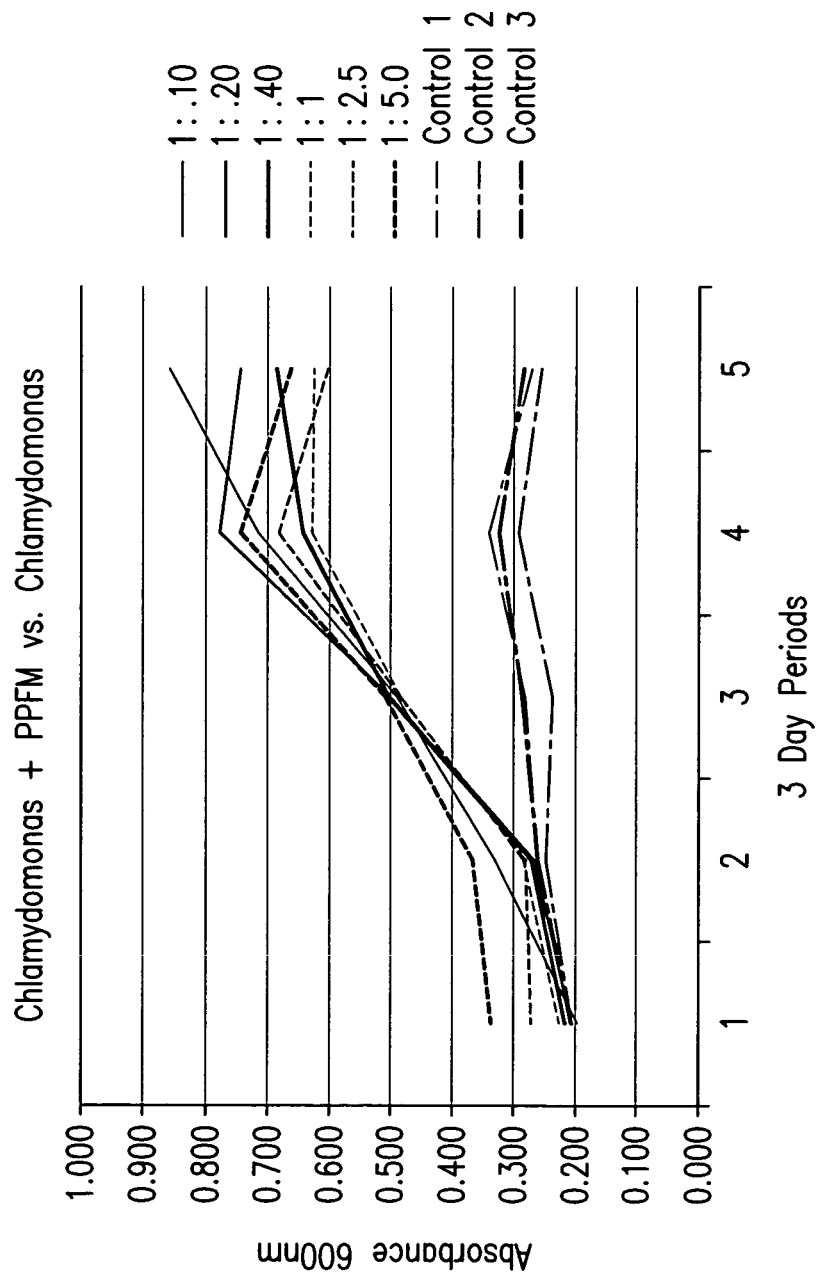
FIG. 1 illustrates a comparison of the effect of co-cultivation of the algae Chlamydomonas and PPFM bacteria versus cultivation of Chlamydomonas alone on algal growth measured over increments of three days. Increased Absorbance 600 nm indicates increased algal growth.
Figure 2:
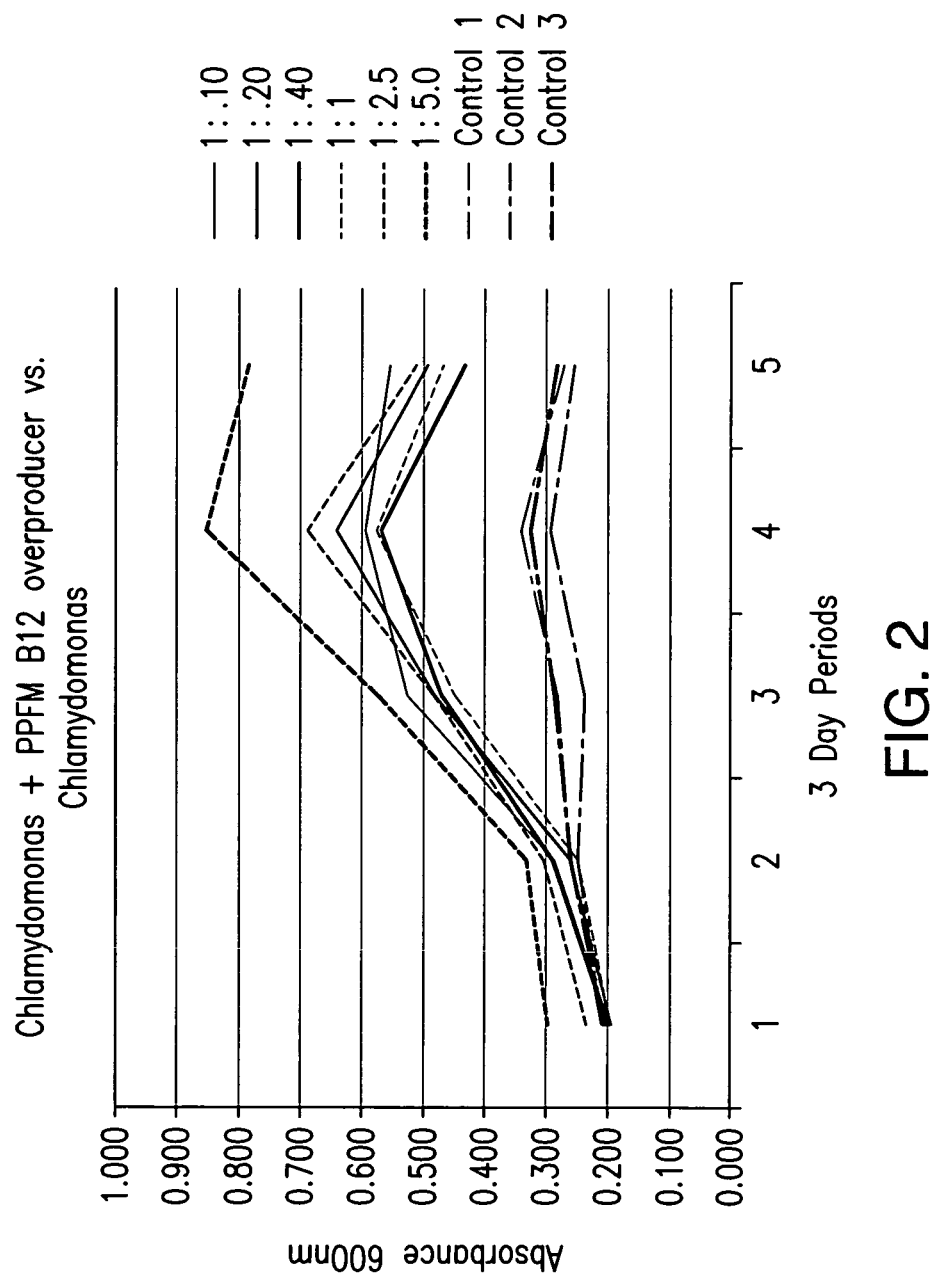
FIG. 2 illustrates a comparison of the effect of co-cultivation of Chlamyodomonas and a PPFM mutant that is a vitamin B-12 overproducer, versus cultivation of Chlamyodonas alone, on algal growth measured over increments of three days. Increased Absorbance 600 nm indicates increased algal growth.
Figure 3:
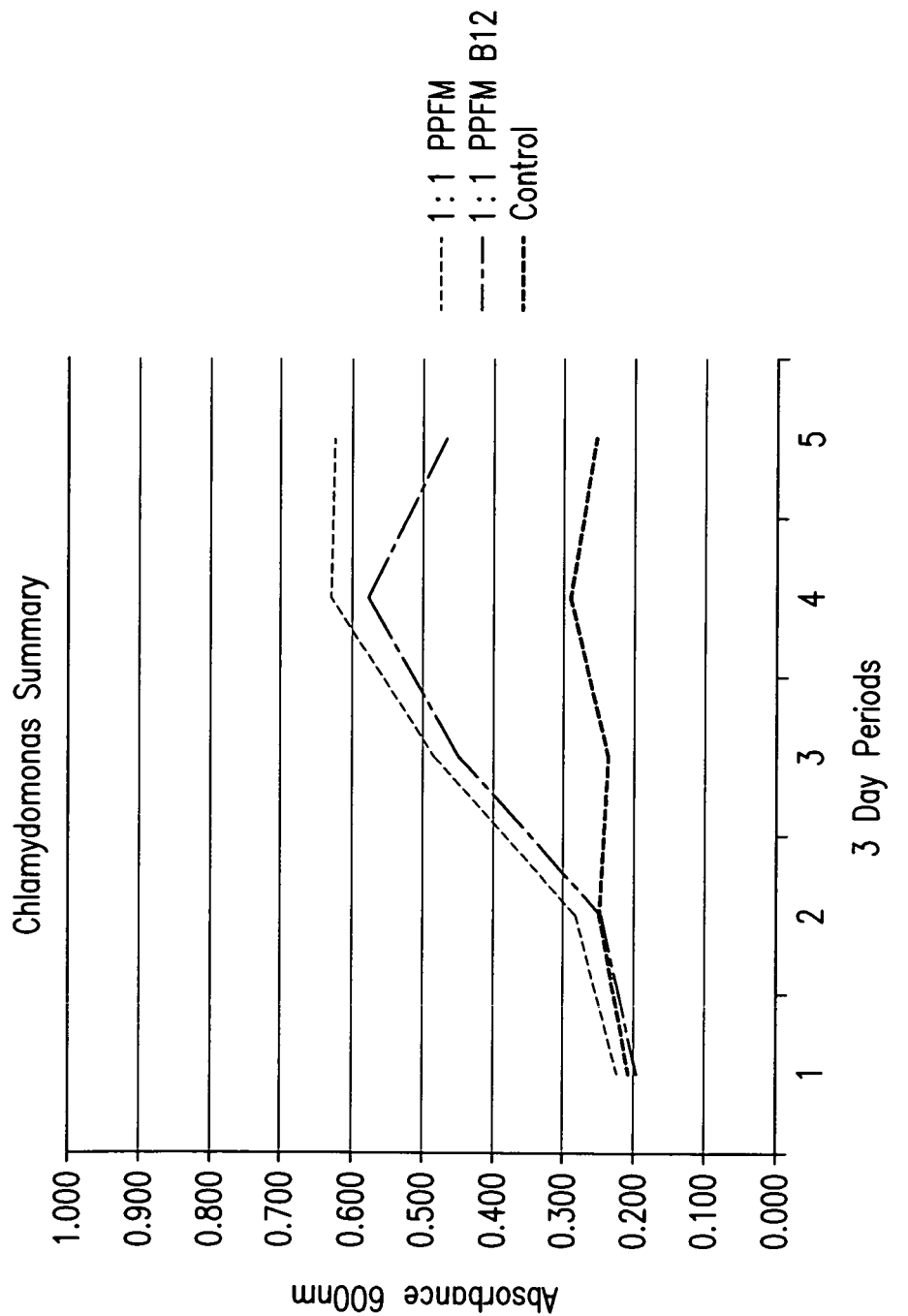
FIG. 3 illustrates a summary of Chlamyodonas growth experiments measured over increments of three days. Increased Absorbance 600 nm indicates increased algal growth.
Figure 4:
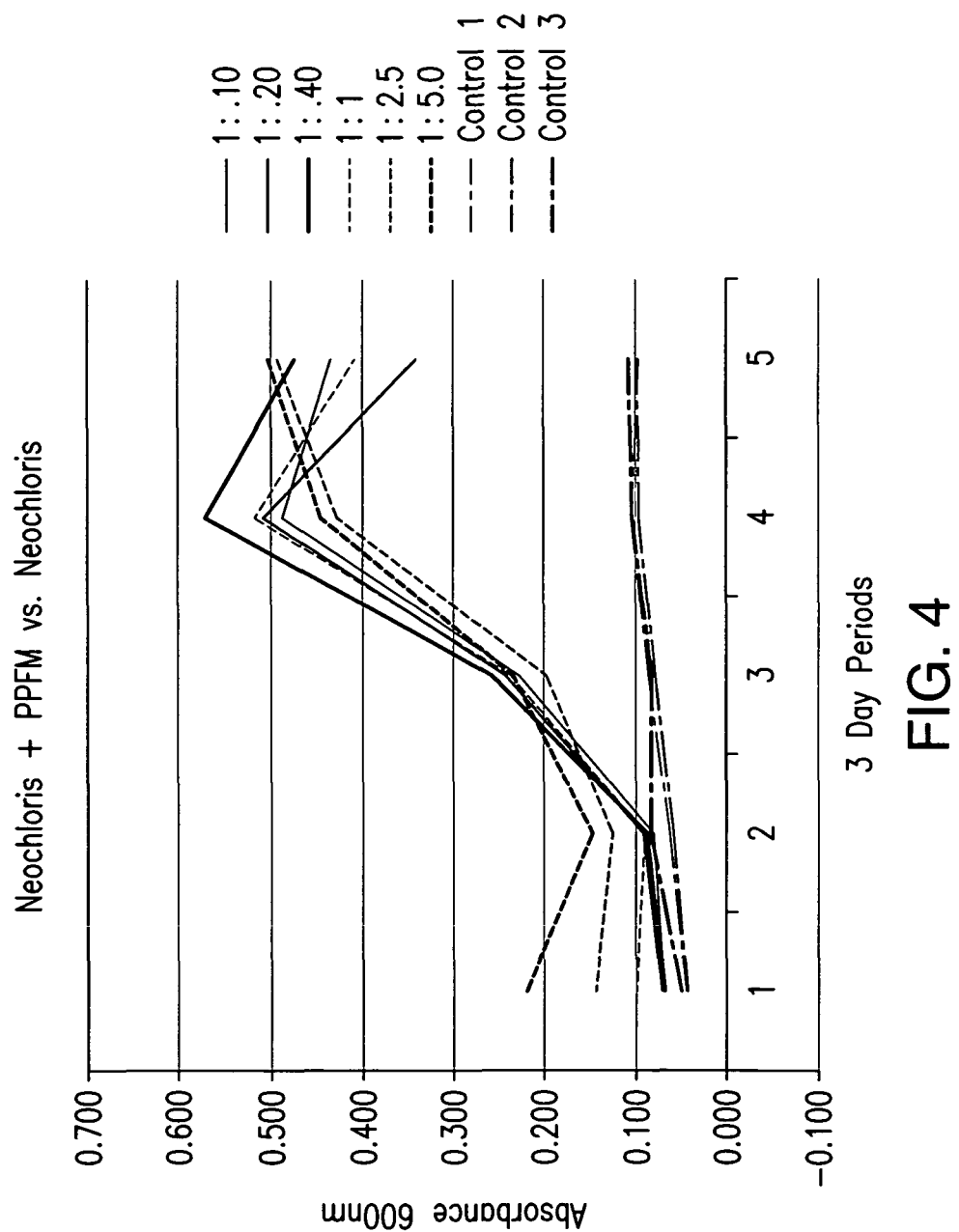
FIG. 4 illustrates a comparison of the effect of co-cultivation of *Neochloris oleoabundans* and PPFM bacteria versus cultivation of *Neochloris* alone, on algal growth measured over increments of three days. Increased Absorbance 600 nm indicates increased algal growth.
Figure 5:
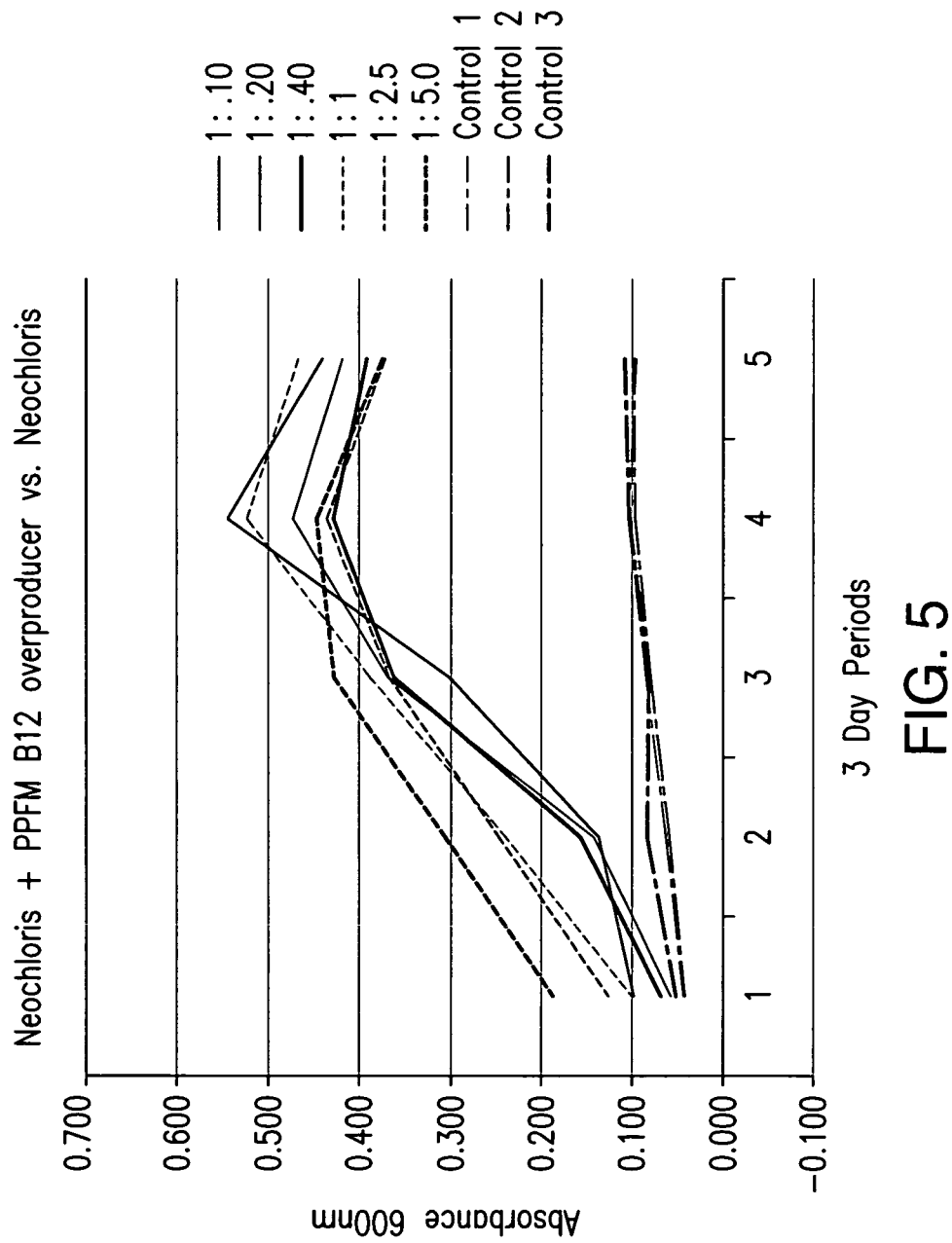
FIG. 5 illustrates a comparison of the effect of co-cultivation of *Neochloris oleoabundans* and the PPFM vitamin B12 overproducer versus cultivation of *Neochloris* alone, measured over increments of three days. Increased Absorbance 600 nm indicates increased algal growth.
Figure 6:
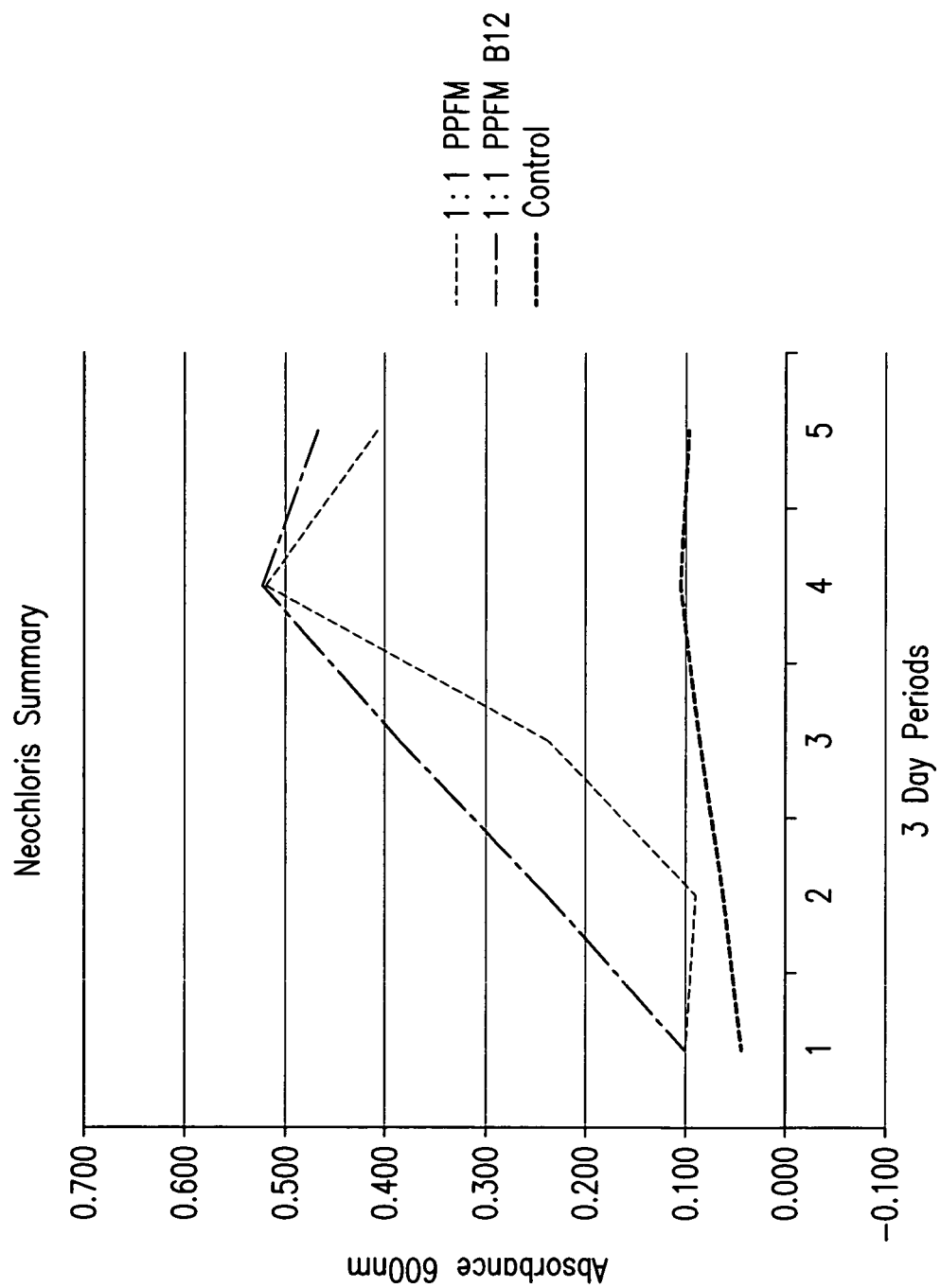
FIG. 6 illustrates a summary of *Neochloris* growth experiments measured over increments of three days. Increased Absorbance 600 nm indicated increased algal growth.

The present invention is based, at least in part, upon the novel discovery that algae growth can be increased or stimulated by co-cultivation of the algae with PPFM bacteria. The PPFM bacteria used may be one or more species thereof, or may be a single strain of a single species thereof. For example, any species of Methylobacteria may be used, such as *M. adhaesivum, M. aminovorans, M. aquaticum, M. chloromethanicum, M. dichloromethanicum, M. extorquens, M. fujisawaense, M. hispanicum, M. isbiliense, M. lusitanum, M. mesophilicum, M. nodulans, M. organophilum, M. podarium, M. populi, M. radiotolerans, M. rhodesianum, M. rhodinum, M. suomiense, M. thiocyanatum, M. variable* and *M. zatmanii*. All of the above are Methylobacters that are facultative methylotrophs, and which produce a pink pigment. The pink pigmentation is the primary diagnostic characteristic used in the initial identification of methylobacteria. Methylobacteria are distributed widely in soil associated with plants, as well as on plants. Procedures for isolating and characterizing Methylobacteria species are well known. See for example, FEMS Microbiol. Ecol. 2004 Mar. 1; 47 (3): 319-26.

While any of the above PPFM species may be used in accordance with the present invention, it has been found particularly advantageous to use *M. mesophilicum* in co-cultivation with algae in the present invention.

As used herein, the term "algae" may mean any type of micro- or macroalgae, but more preferably the term means algae of the genii of *Protococcus, Ulva, Codium, Enteromorpha, Neochloris* and/or *Chlamydomonas*. Micro- and macroalgae, including those of the genii noted above, may be easily collected at seashores in the United States. For example, for the experiments described hereinbelow, various species of the genii *Protococcus, Ulva, Codium* and *Enteromorpha* were collected from fresh water and salt water sources in Salisbury, Md., Assateague National Seashore and at Ocean City, Md. After collection, the algae were placed on petri dishes of ammonium mineral salts (AMS)—medium, selective for the PPFM bacteria. All specimens of algae collected were found to have PPFM bacteria associated with them. This is a surprising finding in that one would not expect a plant-associated bacterial species to be associated with algae, which in general are unicellular or oligocellular.

In particular, however, an important aspect of the present invention entails the co-cultivation of PPFM vitamin B-12 overproducers with those species or strains of algae that happen to be responsive to the presence of vitamin B-12 in the environment. As used herein, the term "PPFM vitamin B12 overproducer" means a PPFM bacteria that produces more vitamin B-12 than a conventional wild-type PPFM. Such PPFM vitamin B-12 overproducers may either be genetically manufactured or naturally selected. If naturally selected, the PPFM vitamin B12 overproducers are mutants of the wild-type, and may be considered as PPFM vitamin B12 mutants.

Generally, any of the selection procedures and particular strains of U.S. Ser. No. 11/347,579, which is incorporated herein in its entirety, may be used in accordance with the present invention.

For example, there are naturally-occurring mutants of PPFM bacteria that overproduce vitamin B-12 based on their ability to stimulate the growth of Arthrobacter (ATCC #12834), a B-12 auxotroph. As described in U.S. Ser. No. 11/347,579, thirty-six (36) putative mutants were initially selected, which were reduced to seventeen (17) upon re-screening. Culture supernatants from these isolates were assayed for vitamin B-12 content by the microbiological method of Capps et al. (J. Biol. Chem. 178:517, 1949) using a commercial B12 assay medium (Difco #0360) and *Lactobacillus delbrueckii* susp. *Lactis* ATCC#4797. The results of this assay are shown in Table 1 below for 17 selected strains of PPFM:

TABLE 1

Vitamin B-12 content of PPFM culture supernatants
(ng vitamin B-12/ml culture medium)

| Strain # | ng B12/ml |
|---|---|
| 1 | 5.4 |
| 2 | 4.2 |
| 4 | 5.8 |
| 5 | 5.7 |
| 6 | 5.9 |
| 7 | 6.2 |
| 8 | 6.9 |
| 9 | 6.5 |
| 10 | 7.5 |
| 11 | 15.0 |
| 13 | 5.5 |
| 15 | 7.5 |
| 21 | 8.0 |
| 26 | 4.2 |
| 29 | 5.0 |
| 32 | 6.0 |
| 34 | 4.9 |

Among the B-12 overproducing mutants isolated, #11, as shown in Table 1, was a standout, producing three times the amount of B12 produced by the other isolates. This organism, designated Methylobacterium mutant B 12-11, was deposited with the American Type Culture Collection (ATCC) in Manassas, Va., on Apr. 4, 2000, under the provisions of the Budapest Treaty. The deposit will be maintained and made available pursuant to the Treaty.

However, it is explicitly contemplated that one skilled in the art is able to screen and isolate other PPFM vitamin B-12 mutants and use the same methods as described herein. Yet, it is not necessary to use any of the B-12 mutant strains of the PPFMs. Algae that might happen to be stimulated by vitamin B-12 are, nevertheless, responsive to PPFMs that are not oversecretors of B-12. And, of course, not all algae species or strains are responsive to vitamin B-12 in the first place.

PPFM bacteria increase the growth rate and the biomass of land plants. PPFM bacteria also encourage growth of land plants by supplying plant growth regulators (cytokinin and auxin), vitamins, amino acids and/or some enzymes. Further, a high proportion of microalgae have an obligate requirement, i.e., are auxotrophic, for vitamin B-12 (cobalamin), and even those algae that are not B 12 auxotrophs take up vitamin B-12 in culture. In some plants, vitamin B-12 may act as a cofactor for enzymes that catalyze either rearrangement-reduction reactions or methyl transfer reactions.

The present invention will now be further illustrated by certain examples, which are provided solely for purposes of illustration and are not intended to be limitative.

Example 1

Liquid cultures were established in the laboratory from the algae specimens collected to include three experimental treatments, which were:

A control of *Protococcus* in water;
1) *Protococcus* in water supplemented with 0.5% methanol, which is known to stimulate growth of PPFM bacteria; and
2) *Protococcus* in water supplemented with a Vitamin B12 overproducing PPFM.

The growth of the cultures was monitored at Absorbance 550 nm with the results below in Table 2 being obtained:

TABLE 2

| A550 nm treatment | Control | Methanol | Vitamin B12-secreting PPFM |
|---|---|---|---|
| Start | 0.073 | 0.069 | 0.075 |
| After One Week | 0.089 | 0.094 | 0.145 |
| After Two Weeks | 0.068 | 0.085 | 0.188 |

Clearly, a dramatic boost in growth is observed in algae cultures containing a vitamin B-12 overproducing PPFM.

The use of algae as a raw material for the production of neutral lipids, i.e., oil, is advantageous for many reasons.

First, the oil yield (L/ha) for algae, per land area required (ha), far surpasses such yields from other raw materials. This is well illustrated below in Table 3:

TABLE 3

| Crop | Oil Yield (L/ha) | Land Area Needed For 530 Billion L |
|---|---|---|
| Soybean (oil) | 446 | 1,188 Million ha |
| Corn (ethanol) | 4,000 | 132.5 Million ha |
| Oil Palm (oil) | 5,950 | 92 Million ha |
| Switch Grass (ethanol) | 7,600 | 69.7 Million ha |
| Sugar Cane (ethanol) | 8,000 | 66.3 Million ha |
| Microalgae-20% (oil) | 35,202 | 15.2 Million ha |
| Microalgae-40% (oil) | 70,405 | 7.6 Million ha | ha = hectares.

Second, algae can be grown anywhere, including in the desert. Thus, algae farms need not compete with edible crops for growing space.

Third, algae represents a non-foodstuff for humans, and, hence, avoids the diversion of foodstuffs to make fuel.

Example 2

Two types of algae, *Chlamyodonas* and *Neochloris oleoabundans*, were inoculated with varying amounts of a wild-type PPFM or with a PPFM B 12 overproducer. Growth of algae was measured over 15 days with a spectrophotometer. The results are illustrated in FIGS. 1-6.

The data from those two experiments show that (1) co-cultivation of Chlamyodonas with a PPFM vitamin B-12 overproducer or with a wild-type strain results in a greater yield of algae over a unit time period, i.e., faster growth and higher cell density; and that (2) co-cultivation of *Neochloris oleoabundans* with a wild-type PPFM strain results in a greater yield of algae over a unit time period.

Figure 7:
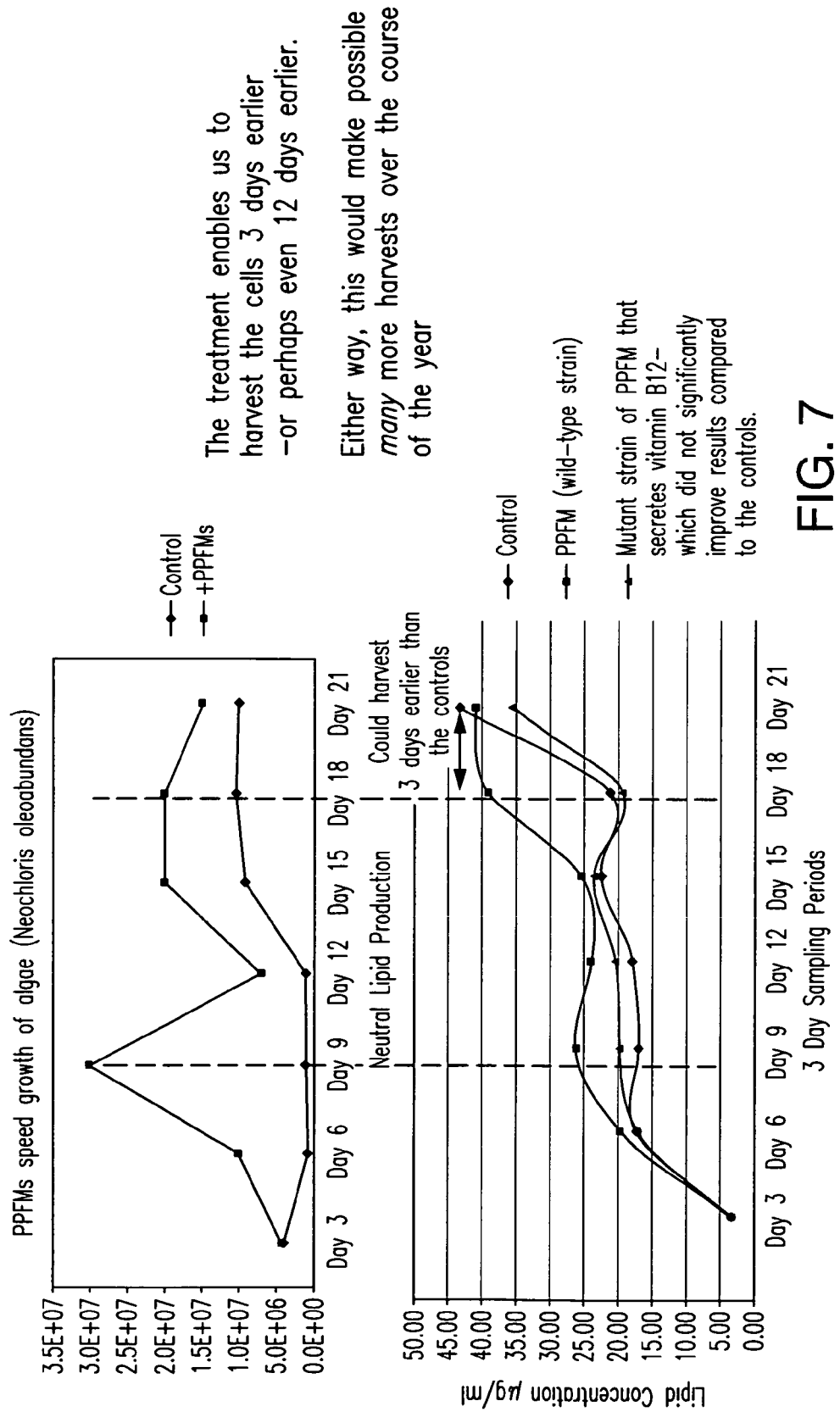
FIG. 7 illustrates that the use of PPFM bacterial inoculants greatly increases yields of algae for biodiesel fuel production.

Further, co-cultivation of *Neochloris oleoabundans* with the wild-type PPFM also increased the yield of neutral lipid from the algae. See FIG. 7.

Figure 8:
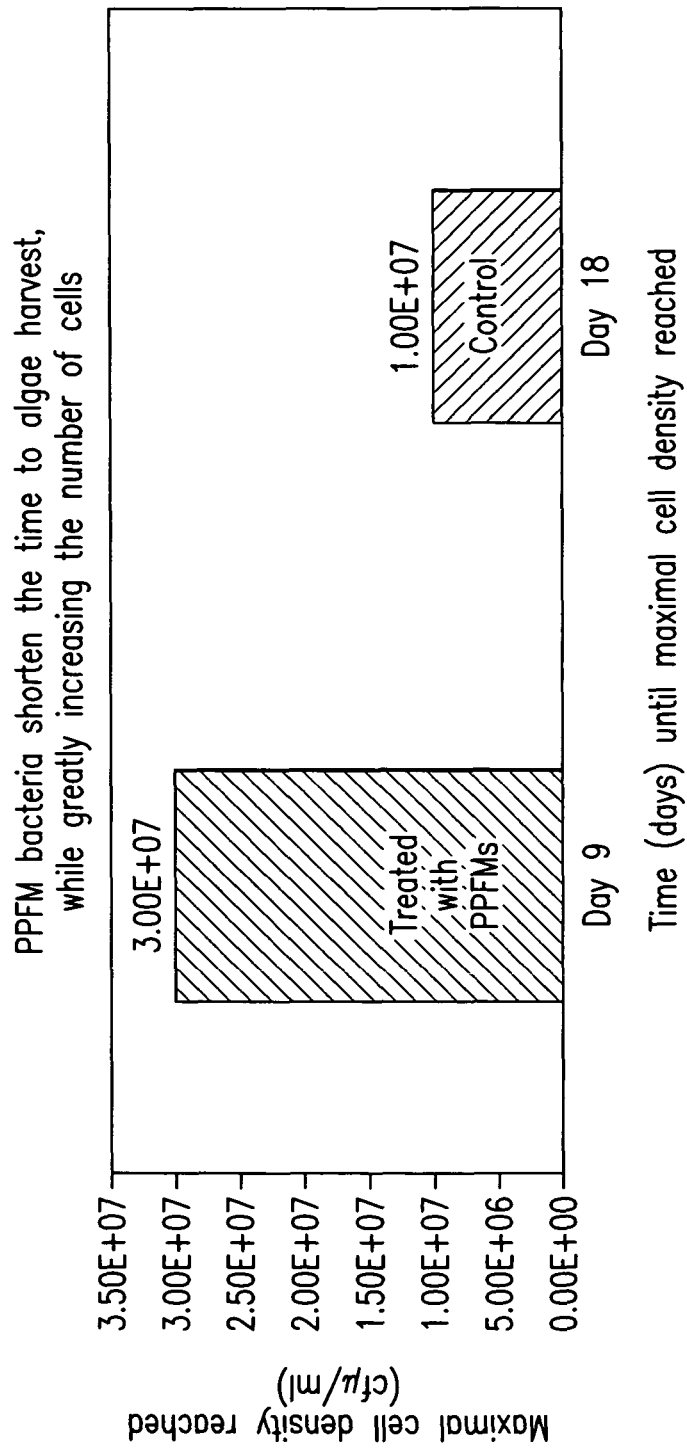
FIG. 8 illustrates that PPFM bacteria shorten the time to algae harvest, while also greatly increasing the number of algae cells harvested.
Figure 9:
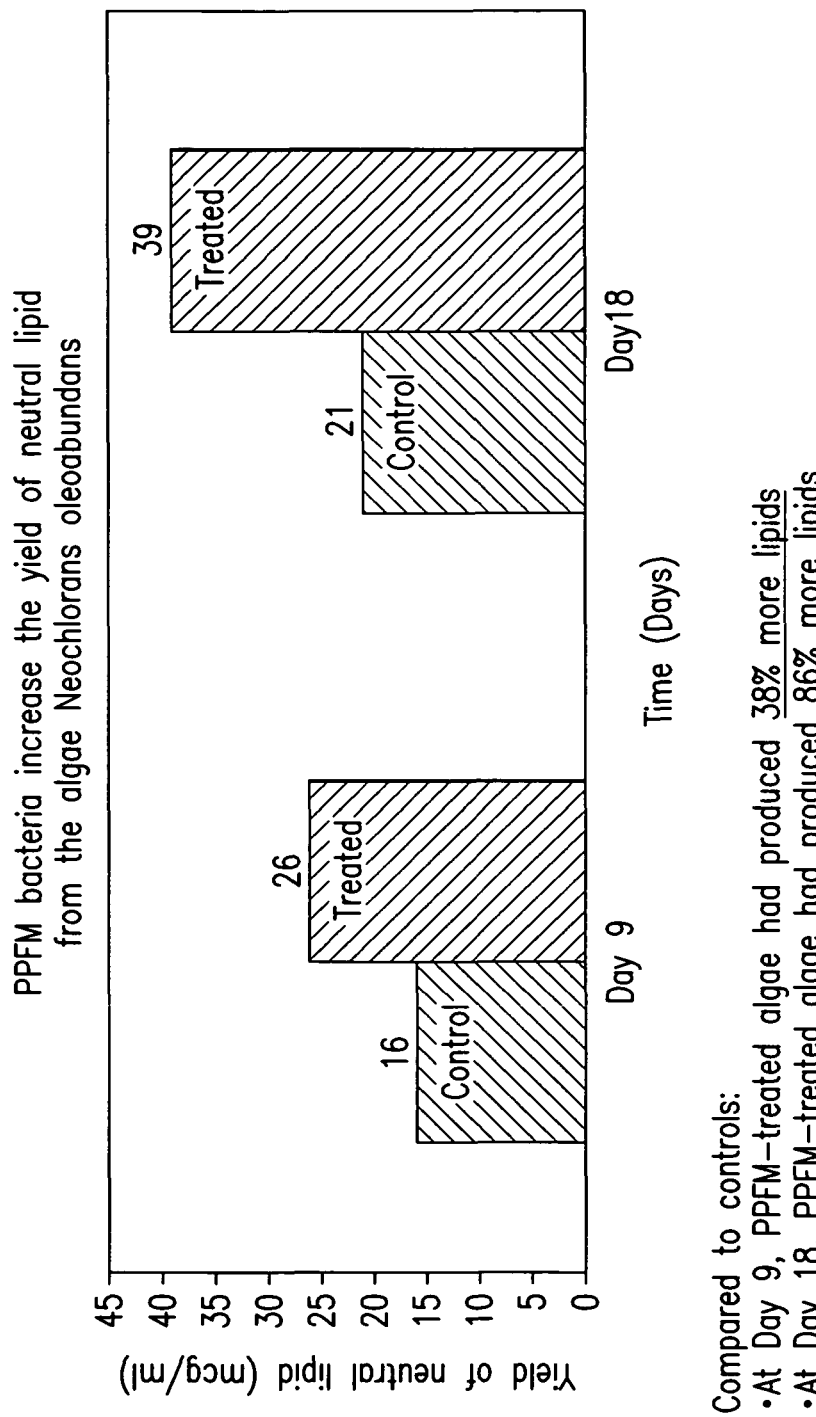
FIG. 9 illustrates that PPFM bacteria increase the yield of neutral lipid from the algae *Neochlorans oleoabundans*.

As indicated above, use of PPFM bacteria shorten the time to algae harvest, while greatly increasing the number of algae cells harvested. See FIG. 8.

Although it is known that inoculating algae with cytokinin will increase the growth rate of the algae, nevertheless the literature indicates that cytokinin does not increase the production of oils or lipids from the algae. See Ordog, et al, Journal of Phycology, Vol. 40, Issue 1, page 88 (February 2004). This strongly suggests that the PPFMs are doing more to stimulate algae metabolism than would be predicted simply from their secretion of cytokinin.

The increased quantity of neutral lipids produced as a result of co-cultivation of algae with PPFMs may be recovered using any well known separation techniques which effect separation of oil from water phases. The recovered oil may be converted to useful diesel fuel by any known process, such as those described in U.S. Pat. Nos. 7,553,982, and 7,905,930, which are both incorporated herein in the entirety.

There are other and additional biofuels that can be extracted/converted from algae and where the yield of such additional biofuels would be commensurately increased if the algal cell density were higher, and/or if the treated algae had, as a result of the PPFM treatment, more energy (as ATP) or other physiological/phenotypic attributes that enabled the algae cells to produce larger quantities of the biofuels. The list of such additional biofuels includes, but is not limited to, ethanol, butane and other hydrocarbons.

While the ability of PPFMs to increase biofuel production is of particular importance to the world economy, there are several other uses to which the present invention may be applied.

First, the present invention affords an increased harvest size, i.e., increased algal cell density, as well as a shorter time-to-harvest of the algal strains that are used (whether whole or in fractions) as fish food, shellfish food, animal food or human food, such as spirulina, chlorella or blue-green algae, for example.

Second, the present invention also affords an increased production of valuable components of algal cells. An exemplary illustrative list of such valuable components, whose yield would be higher due to the co-cultivation of the algae with PPFMs, includes agar, alginate and carrageenan, astaxanthin, beta-carotene, co-enzyme Q10, cosmetics, fertilizers, hydrocolloids andomega fatty acids—(including DHA, which is of key importance in early childhood development).

TERM DEFINITIONS

The following terms and phrases used throughout the specification are as defined below:

"PPFM" means pink-pigmented facultative methylotrophs.

"Absorbance" means spectrophotometric absorbance measured in a conventional manner.

"overproduce" means a bacteria that produces more of a particular substance than a wild-type of the same bacteria. The "overproducer" may be a genetic recombinant or a naturally-selected bacterial strain.

"increased yield" means either an increased yield of algae over unit time relative to a control, or means obtaining the same yield as that of a control but in less than unit time relative to the control.

"unit time" means a required or designated period of time for algae growth. This is also referred to the specification as "cultivation time". Algae are the fastest growing photosynthesizing unicellular organism, and can complete an entire growing cycle every few days. Some algae species have a high oil content (up to 60% by weight) and can produce up to 15,000 gallons of oil per year under conventional optimal conditions.

"chemostat" means a bioreactor to which fresh medium is continuously added, while culture liquid is continuously removed to keep the culture volume constant. One of the most important features of chemostats is that micro-organisms can be grown in a steady state. See U.S. Pat. No. 7,687,261, pertaining to chemostats, which is incorporated herein in its entirety.

"algae bioreactor" means a bioreactor that is used for cultivating algae, and may be of three general types, which are: plate photobioreactor, tubular photobioreactor and bubble column photobioreactor. See U.S. Published Patent Application 2007/0092962, which is incorporated herein by reference in the entirety.

"algae farm" means a larger-scale facility for cultivating algae, where algae is cultivated in many mounted cylinders or shallow pools in a variety of shapes, such as circular, square or rectangular.

"about" as used herein means±1-2%. Thus, the phrase "about 10%" means from about 8-12%.

The present invention may be practiced in a conventional algae bioreactor using a chemostat or in conventional algae farm with multiple ponds. For example, a facility like that of PetroSun in Texas with over 150 separate ponds on over 1,800 acres may be used.

There are many advantages of deriving biodiesel from algae, such as rapid algal growth rate, high per-acre yield and the fact that algal biofuel contains no sulfur, is non-toxic and is highly biodegradable. The projects taking advantage of these merits range from small do-it-youself kits at home available from Free Energy News Store to large commercial facilities, such as the PetroSun facility noted above.

There are many methods known for extracting oil from algal wet mass. Generally, however, any extraction process entails harvesting algae from growth medium by any conventional raking or culling process, and then extracting oil from the harvested algae by mechanical or chemical methods, all of which are known.

As a mechanical process for oil extraction, expression/expeller press or ultrasonic-assisted extraction may be mentioned. As a chemical process for oil extraction, hexane solvent method, Soxhlet extraction or supercritical fluid extraction may be noted.

Hexane extraction is advantageous as less expensive than supercritical extraction, and it can be used alone or in conjunction with the press/expeller (mechanical) method. For example, after oil has been extracted from the algae with an expeller, the remaining pulp can be mixed with cyclohexane to extract the remaining oil content. The oil dissolves in the cyclohexane, and pulp is filtered out of the mixture. It has been reported that the combined techniques of cold press and hexane solvent extraction remove more than 95% of the oil present in the algae.

Additionally, an extraction method, such is described in U.S. Published Patent Application 2009/0029445, which is incorporated herein in its entirety, may also be used.

Currently, the algal biofuel industry is expending considerable effort to improve oil extraction efficiency from algae. Some recent developments in oil extraction include use of steam or ultrasonics to rupture algal cell walls to release more oil for extraction. Similar attempts have been made by subjecting wet algal mass to microwaves, or even using focused light from a parabolic concentrator to rupture algal cell walls.

In accordance with the present invention, any one or combination of the above techniques may be used to obtain oil from algae.

Oil obtained from algae compares well with conventional diesel fuel for several reasons:

1) Algal biodiesel has virtually no sulfur content.
2) Algal biodiesel has superior lubricating properties, reducing fuel system wear, and increases the life of fuel injection equipment.
3) Algal biodiesel has a comparable fuel efficiency with conventional diesel.
4) Algal biodiesel has a flash point (266° F.) that is considerably higher than that of conventional diesel (147° F.) or gasoline (52° F.).
5) Advantageously, algal biodiesel, as noted above, can be produced in quantity at any location with sufficient sunshine.

In a preferred embodiment, PPFMs are freely mixed with and suspended in media in which the algae is cultivated. In another preferred embodiment, PPFMs may be isolated in a chemostat in order to prevent direct contact between the PPFMs and the algae, but wherein compounds secreted by the PPFMs are able to reach the algae in an algal growth medium compartment.

The present invention affords a principal advantage of providing a higher yield of algae growth relative to a control over the same unit time, or of providing the same or similar yield of algae growth relative to a control in less time. The improvement in yield in each case is generally at least about 10%, and in many instances even more. Such improvements afford vast advantage when considering the rapid growth rate of algae under conventional conditions, as well as the high oil content of algae.

Having now described the present invention, it will be clear that many changes and modifications may be made to the above-described embodiments without departing from the spirit and scope of the present invention.

What is claimed is:

1. A method of increasing yield of cultivated *Neochloris oleoabundans*, which comprises the step of cultivating *Neochloris oleoabundans* in the presence of one or more species of Pink Pigmented Facultative Methylotroph (PPFM) bacteria, for at least a portion of the *Neochloris oleoabundans* cultivation.

2. The method of claim 1, wherein the increased yield is measured by increased *Neochloris oleoabundans* cell density at standard harvest time for *Neochloris oleoabundans*.

3. The method of claim 1, wherein the increased yield is measured by a reduced time-to-harvest for a desired *Neochloris oleoabundans* density.

4. The method of claim 1, wherein an increased yield of neutral lipid is obtained compared to the yield of neutral lipid from *Neochloris oleoabundans* grown without PPFM.

5. The method of claim 1, wherein the one or more species of PPFM is a species of *M. mesophilicum*.

6. The method of claim 1, which further comprises isolating neutral lipids from said *Neochloris oleoabundans*.

7. The method of claim 6, wherein the neutral lipids are further used as feedstock for oil for biodiesel.

8. The method of claim 6, wherein the neutral lipids are further used as feedstock for ethanol.

9. The method of claim 6, wherein the neutral lipids are further used as feedstock for butane or other hydrocarbons.

10. The method of claim 1, which further comprises isolating the cultivated *Neochloris oleoabundans* for subsequent use for animal or human consumption.

11. The method of claim 1, which further comprises isolating one or more compounds from the cultivated *Neochloris oleoabundans*, wherein the compound(s) are agar, alginate, astaxanthin, beta-carotene, carrageenan, coenzyme Q10, or docosahexaenoic Acid (DHA).

12. The method of claim 1, which is conducted in an outdoor facility.

13. The method of claim 12, wherein the outdoor facility is a pond.

14. The method of claim 1, which is conducted in an indoor photo-bioreactor.

15. The method of claim 12, wherein the PPFMs are freely mixed with and suspended in media in which the *Neochloris oleoabundans* are cultivated.

16. The method of claim 13, wherein the PPFMs are freely mixed with and suspended in media in which the *Neochloris oleoabundans* are cultivated.

17. The method of claim 12, wherein the PPFMs are isolated in a chemostat in order to prevent direct contact between the PPFMs and the *Neochloris oleoabundans*, but wherein compounds secreted by the PPFMs are able to reach the *Neochloris oleoabundans* in an algal growth medium compartment.

18. The method of claim 17, wherein the secreted compounds are able to reach the algal growth compartment by being pumped directly into the compartment.

19. The method of claim 17, wherein the secreted compounds are able to reach the algal growth compartment by free diffusion of the secreted compounds across tubing into the compartment.

20. The method of claim 1, which produces a maximum density that is at least about 10% greater than a control in a same unit time.

21. The method of claim 1, which produces a maximum density that is the same as a control, but in at least about 10% less unit time.

22. The method of claim 1, wherein the co-cultivation of the *Neochloris oleoabundans* one or more species of algae with one or more species of PPFM bacteria is for an entire cultivation time.

* * * * *